United States Patent [19]

Whitney

[11] 4,220,151
[45] Sep. 2, 1980

[54] DISPOSABLE LUER LOCK SYRINGE

[75] Inventor: Edgar H. Whitney, Seminole, Fla.

[73] Assignee: Sherwood Medical Industries Inc., St. Louis, Mo.

[21] Appl. No.: 944,225

[22] Filed: Sep. 20, 1978

[51] Int. Cl.³ .............................................. A61M 5/00
[52] U.S. Cl. ................................. 128/218 N; 128/221
[58] Field of Search .............. 128/218 N, 218 R, 221, 128/215, 216

[56] References Cited

U.S. PATENT DOCUMENTS

| | | | |
|---|---|---|---|
| 2,834,346 | 5/1958 | Adams | 128/218 R |
| 3,301,256 | 1/1967 | Cowley | 128/218 N |
| 3,306,291 | 2/1967 | Burke | 128/218 R |
| 3,320,954 | 5/1967 | Cowley | 128/218 N |
| 3,402,713 | 9/1968 | Senkowski et al. | 128/221 |
| 3,542,024 | 11/1970 | Burke | 128/221 |
| 3,638,650 | 2/1972 | Burke et al. | 128/221 |
| 3,712,302 | 1/1973 | Burke et al. | 128/221 |
| 4,027,669 | 6/1977 | Johnston et al. | 128/218 N |

Primary Examiner—John D. Yasko
Attorney, Agent, or Firm—Stanley N. Garber; William R. O'Meara

[57] ABSTRACT

A disposable Luer lock syringe is provided with an integral Luer tapered needle connector and an integral, internally threaded, Luer lock retaining collar surrounding the connector and having a plurality of circumferentially spaced, longitudinal grooves. The grooved collar is circumferentially continuous and has sufficient rigidity for obtaining a desired fluid-tight connection with the hub of a needle assembly, while the grooves provide the collar with sufficient flexibility to permit the fracturing of the connector after the syringe is used so as to prevent reuse of the syringe.

29 Claims, 6 Drawing Figures

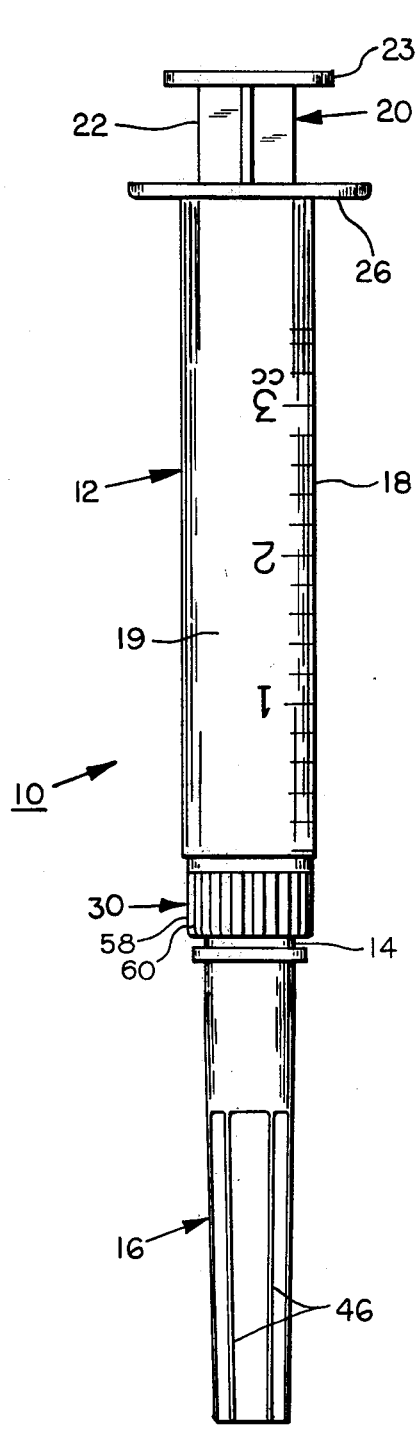
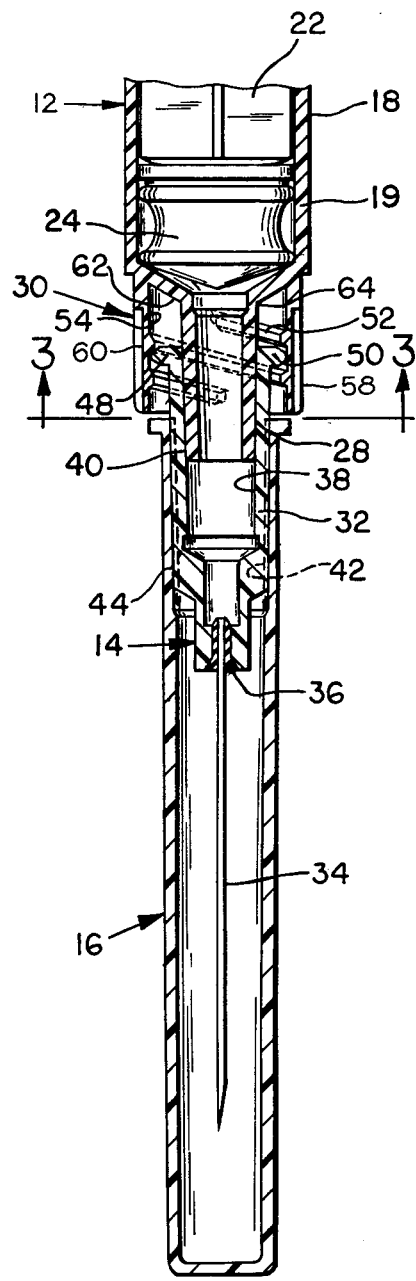
FIG. 1
FIG. 2

DISPOSABLE LUER LOCK SYRINGE

BACKGROUND OF THE INVENTION

This invention relates to disposable Luer lock syringes and more particularly to a disposable Luer lock syringe that can be altered after use to prevent reuse.

It is generally desirable to alter disposable or single-use plastic hypodermic syringes after use in a manner that prevents reuse of the syringe. For example, the syringe tip or Luer needle connector that is adapted to receive a needle hub may be conveniently and safely fractured or broken away from the syringe barrel by employing the needle hub and sheath to bend and fracture the connector. However, where the distal end of the syringe is provided with a Luer lock construction, the threaded Luer lock collar surrounding the needle connector generally hinders and, in some cases, prevents sufficient angular or lateral bending movement of the connector for effectively fracturing it. This is especially the case where the Luer lock syringe barrel is made of polypropylene, which plastic is commonly used because of its inertness to fluid typically used in syringes but which is a relatively tough material.

One of the problems of making a Luer lock syringe that can be readily and effectively destroyed after use has been that, if the collar was made sufficiently flexible to readily allow fracturing of the connector, it was generally too weak to obtain a desired fluid-tight connection between the hub and connector by rotating the hub relative to the collar. For example, the hub ears which engage the threads of the collar may cause such a collar to distort and slip the threads as the hub is rotated before enough torque can be applied for obtaining the desired fluid-tight connection.

SUMMARY OF THE INVENTION

Accordingly, it is an object of the present invention to provide a syringe having a Luer lock collar surrounding a Luer tapered connector which will provide sufficient rigidity for obtaining a desirable fluid-tight connection with a device to be coupled to the connector, and which will readily permit the destruction of the connector after use to prevent reuse of the syringe.

Another object of the present invention is to provide a method of destroying a connector of a Luer lock syringe having a surrounding Luer lock collar in a relatively easy, effective, and safe manner.

In accordance with one aspect of the present invention, a syringe is provided with a Luer lock collar surrounding a connector and with the collar having structurally weakened portions of reduced thickness to allow bending of the connector sufficiently to fracture it. In accordance with another aspect of the invention, a method of breaking a Luer connector of a syringe having a surrounding Luer lock collar includes employing a needle sheath and needle hub to bend and fracture the collar and connector.

These, as well as other objects and advantages of the present invention, will become apparent from the following detailed description and drawings.

BRIEF DESCRIPTION OF THE DRAWINGS

FIG. 1 is an elevational view of a syringe in accordance with the preferred embodiment of the present invention;

FIG. 2 is an enlarged partial cross-sectional view of the syringe of FIG. 1;

DESCRIPTION OF THE PREFERRED EMBODIMENT

Figure 3:
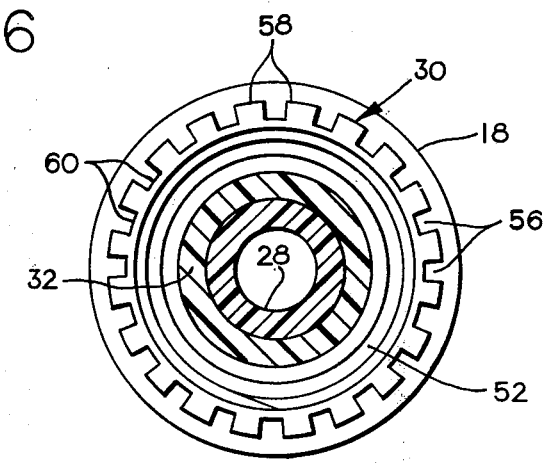
FIG. 3 is an enlarged cross-sectional view taken along the lines 3—3 of FIG. 2.

Referring now to the drawings, and particularly to FIGS. 1-3, a hypodermic syringe assembly 10 is shown including a syringe 12, a conventional needle assembly 14 attached to the distal end of the syringe, and a needle protector or sheath 16 surrounding the needle assembly.

The syringe 12 includes a barrel 18 receiving a conventional plunger 20 which includes a rod 22 having a thumb flange 23 at the proximal end and a rubber piston 24 attached to the distal end of the rod. Barrel 18 has a conventional integral finger flange 26 at the proximal end for facilitating manual movement of the plunger relative to the barrel during use of the syringe. The barrel 18 has a cylindrical main body 19, a Luer tapered syringe tip in the form of an integral Luer tapered needle adapter or connector 28, and an integral Luer lock sleeve or retaining collar 30 surrounding connector 28 in concentric relation at the distal end of the barrel. The connector 28 extends distally beyond the distal end of collar 30.

Preferably, barrel 18 is formed or molded of polypropylene plastic because of its inertness with respect to blood and many chemicals, although in some cases other well known thermoplastic materials may be used. The barrel 18 is a single-piece member with the body 19, connector 28 and collar 30 all integrally connected together.

The needle assembly 14 includes a needle hub 32 carrying a hypodermic needle cannula 34 which is shown connected by a suitable cement 36 to the distal end of the hub. Hub 32 has a Luer tapered inner surface 38 which is rotatably and axially movable into fluid-tight engagement with the Luer tapered outer surface 40 of the needle connector 28 for connecting the interior of the barrel 18 in fluid communication with the needle 34. The connector 28 can be connected in fluid-tight connection with a coupling element other than a needle hub. For example, a catheter or Luer coupling element of a tube connector could be connected to connector 28.

The needle protecting sheath 16 receives the needle 34 and a distal protion of the hub 32. The sheath is provided with longitudinally extending internal grooves 42 which receive longitudinally extending ribs or fins 44 on the exterior of the hub 32 when the sheath 16 is moved axially over the hub 32. When the sheath is rotated, the sidewalls of the grooves 42 and ribs 44 cooperate to effect simultaneous rotation of the hub. The sheath 16, as seen in FIG. 1, is shown provided with longitudinally extending external ribs 46 for facilitating manual rotation of the sheath and hub. The proximal end of hub 32 is provided with a pair of integral, diametrically opposite, radially extending ears 48 and 50. These ears engage Luer lock threads 52 which threads are integrally formed on the interior wall indicated at 54, of the Luer lock collar 30. The threads 52 preferably include a pair of threads which start 180° apart and adjacent the distal end of the collar so that both ears 48 and 50 can be simultaneously started and threaded axially upwardly into the collar 30 when the hub 32, as viewed in the drawings, is rotated clockwise or rightwardly on its longitudinal axis relative to the barrel 18.

When it is desired to effect a fluid-tight connection between the needle assembly 14 and the syringe barrel 18, the sheath 16 is rotated clockwise relative to the barrel to rotate and move the hub 28 axially into tight sealing engagement with the outer Luer tapered surface 40 of the needle connector 28. The engagement between the hub ears 48 and 50 and the collar threads 52 aids in maintaining the fluid-tight connection between the hub and connector. After the needle assembly 14 is tightly connected to the needle connector 28, sheath 16 may be removed and the syringe and needle assembly 14 employed for its intended purpose, for example, to inject a liquid medicament into the vein of a patient. Once the syringe has been put to use, the sheath 16 may be replaced over the needle and hub preparatory to destroying or altering the barrel so that the syringe cannot be reused, as will be discussed hereafter.

Figure 4:
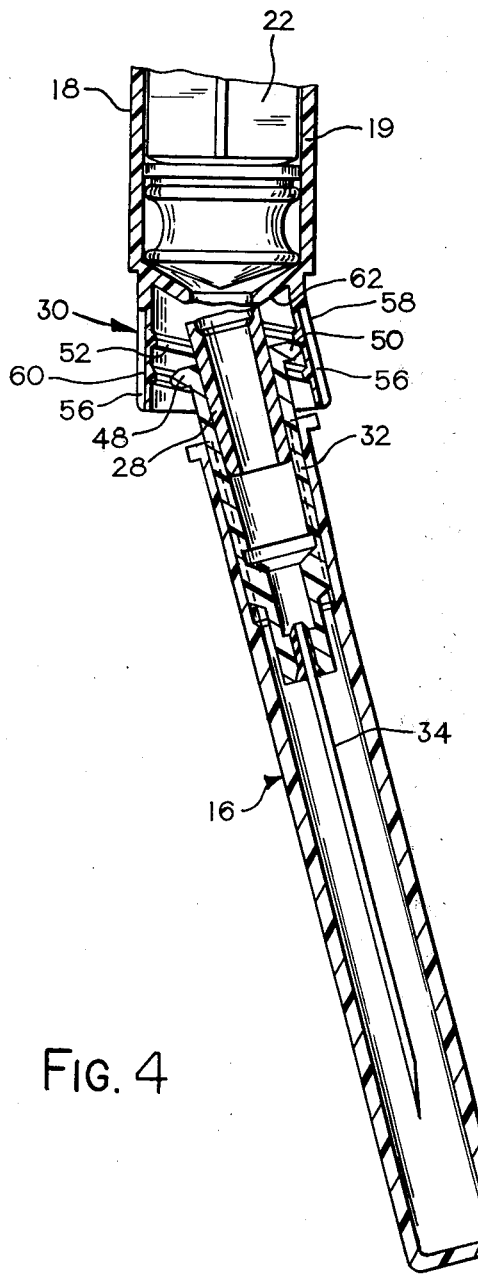
FIG. 4 is a cross-sectional view similar to FIG. 2 but illustrating the syringe during the breaking of the connector portion of the syringe.

The syringe barrel 18 is formed or molded such that the Luer lock collar 30 is strong enough to permit the application of manually applied torques that are sufficient to obtain a good fluid-tight coupling between the connector 28 and the hub 32 such as in the manner discussed above. At the same time, collar 30 is formed so that it is structurally weak enough or flexible enough to permit sufficient lateral or angular movement of the sheath and hub in order to fracture or break connector 28 from barrel 18, such as illustrated in FIG. 4. These desirable characteristics are obtained in the illustrated embodiment by forming the syringe with a plurality of equally circumferentially spaced, like grooves 56 in the radially outer wall of collar 30 which extend generally axially from the distal end of collar 30 toward the barrel body 19. The grooves 56 provide like, equally spaced, relatively strong rigid portions or ribs 58 and relatively weak and flexible portions 60 which form the bottom walls of the grooves 56. The ribs 58 and weak portions 60 alternate circumferentially about the collar 30 and are about equal in width and are shown extending axially or longitudinally substantially to the bottom end wall indicated at 62 in FIGS. 2 and 3 of barrel 8. Also, and as shown in the illustrated embodiment, the collar 30 extends 360° and is circumferentially continuous or without any wall separations.

With the collar 30 circumferentially continuous, and being provided with threads 52 which are each continuous from beginning to end, and relatively rigid ribs 58, the collar is sufficiently strong that relatively high torques can be applied to the hub 32 in obtaining a secure fluid-tight coupling between the connector 28 and the hub. For example, when sheath 16 is rotated clockwise, ears 48 and 50 on the hub will be forced to follow threads 52 and move the hub into tight sealing engagement with the connector 28, and this will occur without the collar 30 becoming distorted such that there is thread slippage.

Figure 5:
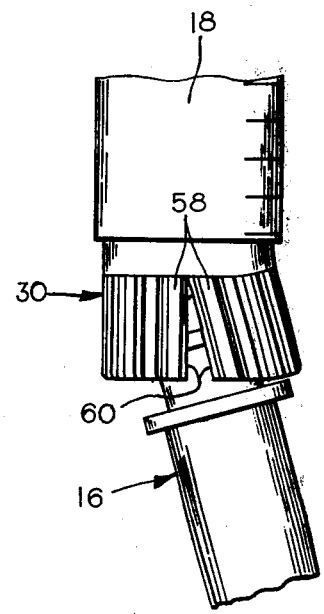
FIG. 5 is a fragmentary elevational view of the syringe in a condition similar to that shown in FIG. 4.

After the syringe 10 has been used for its intended purpose, sheath 16 is preferably replaced on the hub 32, such as in FIG. 2. Then, with one hand grasping the barrel 18 and the other hand grasping sheath 16, the sheath is moved, preferably, with a quick or snap-action movement, laterally or angularly with respect to the longitudinal axis of the barrel to fracture the connector 28 and break it off the barrel 18 as seen in FIG. 4. Because of the weakened areas 60 around the Luer lock collar 30, the collar is flexible enough to allow the hub 32 to be moved angularly by the sheath 16 a distance great enough to fracture or break the connector 28 away from the barrel 18, and without requiring excessive forces. Because each of the weakened portions 60 is relatively thin in cross section compared to the portions or ribs 58 adjacent each side, the collar 30 readily bends outwardly and/or fractures or tears during the above snap-action movement. Preferably, the collar is made to split which makes it generally easy to fracture the connector 28. In FIG. 5 the Luer lock collar 30 is indicated, for illustration, as being split or torn along one of the weakened areas 60. The manner in which the collar flexes and/or splits depends generally upon the way in which the syringe is held and the force applied. In some cases, for example, the collar may split along two weakened portions 60 to bend a section of the collar outwardly. Thus, by providing weakened areas of relatively small cross section, such as portions 60, the collar 30 has sufficient flexibility and/or capability of tearing during the breaking of the needle connector 28, and such that the breakage is accomplished relatively easily.

Generally, where the sheath 16 does not extend into the Luer collar, as in the syringe assembly 10, the side wall of the hub 32 first engages the distal end of collar 30 during the destruction of the barrel. In this way, the collar 30 tears from the distal end toward its proximal end. The distal end of the collar can be made slightly thinner than where it joins the body of the barrel, for example, 0.001 or 0.002 inch, so that the tear is easily started.

It is desirable to fracture the connector 28 so that no usable portion of the connector remains on the barrel, for example, as shown in FIG. 4. In order to facilitate the breaking away of the connector 28 from the barrel 18 and ensure a desirable break location, barrel 18, as shown in FIGS. 2 and 4, is molded such that it has an annular fracturable portion or wall 64 of relatively less thickness than the adjacent wall portions on either side of it. Wall 64 is located within the collar 30 and at or near the junction of the hub and end wall 62 so that the connector 28 breaks away from the barrel body 19, substantially without leaving any suitable connector portion for reuse.

Figure 6:
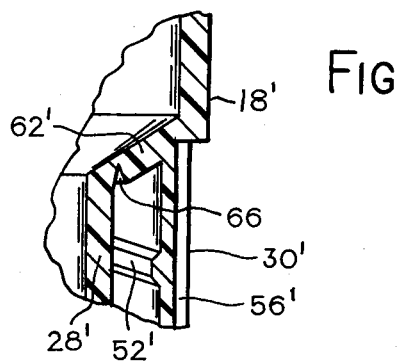
FIG. 6 is a fragmentary cross-sectional view of a syringe having a connector with a modified frangible portion.

In the modified construction shown in FIG. 6, a syringe barrel 18' is shown having an annular groove 66 formed in a barrel end wall 62' at or near the junction of a Luer connector 28' and the end wall. A Luer lock collar 30' is provided with internal threads 52' and longitudinal grooves 26', and is adapted to tear or split at one or more of the grooves during the breaking of the connector from the barrel. The connector 28' separates from the barrel 18' at the groove 66 leaving substantially no effective connector portion for reuse of the syringe barrel 18'.

In one case, a polypropylene barrel was provided with a Luer lock collar 30 having a maximum outer diameter of about 0.357 inch, twenty grooves 56, and twenty ribs 58. The axial length of the collar was about 0.291 inch and the connector 28 about 0.343 inch with the connector having a wall thickness of about 0.038 inch and extending distally beyond the collar about ⅛ of an inch. The threads were 10 pitch and about 0.0195 inch inch high. The wall thickness of the collar through each rib 58 (a point of maximum thickness) was about 0.0235 inch, and that through each bottom wall portion 60, between the ribs (a point of minimum thickness) was about 0.0065 inch. The wall thickness of a weak portion 60 was substantially less than the wall thickness at a rib 58, the portion 60 being between ¼ and ⅓ of the thickness at a rib and substantially less than 1/100 of an inch. With this construction the collar splits or tears such that portions of it bend outwardly to permit a relatively large angular movement of the hub 32 for the purpose of breaking the connector.

In view of the above, it is seen that the several objects and advantages of the invention are achieved and other advantageous results obtained. As various changes could be made in the above construction without departing from the scope of the invention, it is intended that all matter contained in the above description and shown in the accompanying drawings shall be interpreted as illustrative and not in a limiting sense.

What is claimed is:

1. A disposable Luer lock syringe comprising a syringe barrel adapted to receive a syringe piston, said barrel including a plastic Luer tapered connector connected thereto at the distal end thereof for receiving a coupling element of a device adapted for fluid communication with said barrel, a plastic fracturable portion connected to said connector and spaced proximally of the distal end of said connector, and a plastic Luer lock collar connected to said barrel and surrounding said connector and having thread means thereon adapted to threadedly engage portions of the coupling element when the coupling element is received by said connector, said collar having a plurality of circumferentially disposed generally axially extending grooves each having a bottom wall with weak portions of less thickness than the depth of the groove so that weak portions of said collar and said connector can be bent sufficiently to fracture said fracturable portion and prevent effective reuse of the syringe.

2. The syringe of claim 1 wherein said connector and collar are of a thermoplastic material and integrally connected together.

3. The syringe of claim 2 wherein said barrel is an integral, single-piece plastic member.

4. The syringe of claim 1, 2 or 3 wherein said collar is circumferentially continuous.

5. The syringe of claim 4 wherein said plastic comprises polypropylene.

6. The syringe of claim 5 wherein the wall thickness of said relatively weak portions is substantially less than 0.01 inch.

7. The syringe of claim 1 wherein said collar is circumferentially continuous and integral with said connector, and wherein said collar includes relatively rigid ribs on the opposed sides of each of said grooves of greater thickness than said bottom walls and which circumferentially alternate with said grooves.

8. The syringe of claim 7 wherein said barrel is a single-piece plastic member.

9. The syringe of claim 8 wherien said grooves extend proximally from the distal end of said collar.

10. The syringe of claim 9 wherein said grooves extend substantially parallel to the longitudinal axis of said barrel.

11. The syringe of claim 10 wherein each of said weak portions is fracturable and tearable when a selected portion of said collar is sufficiently bent radially outwardly.

12. The syringe of claim 1 or 11 including a coupling element comprising a needle assembly having a hub and a needle cannula connected to said hub, said hub having an inner Luer tapered surface for fluid-tight connection with said connector, and radial extension means on said hub for threaded engagement with said thread means.

13. The syringe of claim 12 further including a needle sheath enclosing said needle cannula and having an open proximal portion surrounding said hub, said hub and said surrounding portion having complementary engagement means whereby rotation of said sheath effects threaded rotation of said hub into tight engagement with said connector, said fracturable portion fracturing and said collar flexing in response to a manually applied force on said sheath causing angular movement of said hub, said connector, and said collar.

14. The syringe of claim 7 or 13 wherein said thread means are continuous from beginning to end.

15. A single-piece syringe barrel of thermoplastic material for a disposable Luer lock comprising a cylindrical main body portion open at the proximal end for receiving a syringe piston, and Luer lock connection means integrally connected to the distal end of said body portion, said connection means including a generally radially inwardly extending end wall at the distal end of said body portion, a Luer tapered connector extending axially from said end wall, a fracturable portion between said body portion and said connector, and an annular flexible Luer lock retaining collar surrounding said connector, said collar having a plurality of generally radially inwardly and axially extending circumferentially spaced grooves in its outer wall in each quadrant thereof defining axially extending ribs on each side of each groove, each of said grooves having a fracturable bottom wall portion with a thickness less than one-half of the thickness of said collar taken through one of said ribs, and thread means on the inner wall of said collar for threaded engagement with a coupling element of a device adapted for connection in fluid communication with the barrel.

16. The barrel of claim 15 wherein said collar is circumferentially continuous and said threads are continuous between the beginning and end thereof.

17. The barrel of claim 16 wherein said thermoplastic material comprises polypropylene.

18. The barrel of claim 16 wherein said connector extends distally beyond the distal end of said collar.

19. A method of effectively destroying a Luer lock syringe having a plastic syringe barrel which has a frangible Luer tapered connector and a frangible Luer lock collar surrounding said connector and having internal thread means, a needle assembly having a hub surrounding the connector and means threadedly engaged with the thread means of the collar, and a needle sheath having a portion surrounding said needle and another portion surrounding said hub, comprising the steps of forming the collar with circumferentially spaced, axially extending radial grooves which extend to the distal end of the collar and having bottom walls of relatively thin plastic material, moving the sheath while surrounding the hub angularly relative to the longitudinal axis of the syringe to fracture and split the collar from the distal end inwardly along a bottom wall of a groove, and continuing to move the sheath angularly to fracture said connector.

20. The method of claim 19 including the step of completely breaking the connector away from the barrel at the fracture by moving said sheath.

21. The method of claim 20 including molding the collar so that the bottom walls of the grooves have portions with a wall thickness of less than 0.01 inch.

22. The syringe of claim 1 including a coupling element having a Luer tapered surface sealably engageable with said connector, and means for moving said coupling element and said connector angularly relative to the longitudinal axis of said barrel to fracture said fracturable portion.

23. The syringe of claim 1 wherein said fracturable portion includes an annular groove at which said fracturable portion is fracturable.

24. The syringe of claim 1 or 13 wherein the thickness of the bottom weak portion of each of said grooves is approximately 0.0065 inch.

25. The syringe of claim 23 wherein the thickness of the bottom wall weak portion of each of said grooves is less than one-third of the maximum thickness of said collar.

26. The syringe of claim 25 wherein said collar is thinnest at its distal end to facilitate the start of a tear during the fracturing of said fracturable portion of said connector.

27. The barrel of claim 16 wherein the thickness of each of said bottom wall portions is less than the depth of each of said grooves.

28. The barrel of claim 27 wherein said collar has approximately twenty of said grooves.

29. The barrel of claim 16 wherein said fracturable portion of said barrel includes an annular groove disposed adjacent the junction of said end wall and said connector.

* * * * *